(12) United States Patent
Yamada et al.

(10) Patent No.: US 10,442,821 B2
(45) Date of Patent: Oct. 15, 2019

(54) METHOD FOR RELEASING UNSATURATED ALDEHYDE OR KETONE

(71) Applicant: TAKASAGO INTERNATIONAL CORPORATION, Ota-ku, Tokyo (JP)

(72) Inventors: Shinya Yamada, Kanagawa (JP); Tadahide Hatakeyama, Kanagawa (JP); Hideki Nara, Kanagawa (JP); Takahiro Ishikawa, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/322,004

(22) PCT Filed: Aug. 1, 2017

(86) PCT No.: PCT/JP2017/027948
§ 371 (c)(1),
(2) Date: Jan. 30, 2019

(87) PCT Pub. No.: WO2018/025882
PCT Pub. Date: Feb. 8, 2018

(65) Prior Publication Data
US 2019/0185494 A1    Jun. 20, 2019

(30) Foreign Application Priority Data

Aug. 1, 2016  (JP) .................................. 2016-151468

(51) Int. Cl.
| | | |
|---|---|---|
| A61K 8/35 | (2006.01) | |
| C07F 7/02 | (2006.01) | |
| A61Q 5/00 | (2006.01) | |
| A61K 8/58 | (2006.01) | |
| A61Q 13/00 | (2006.01) | |
| A61Q 19/00 | (2006.01) | |
| C11B 9/00 | (2006.01) | |
| C11D 3/50 | (2006.01) | |

(52) U.S. Cl.
CPC ................ *C07F 7/025* (2013.01); *A61K 8/35* (2013.01); *A61K 8/58* (2013.01); *A61Q 5/00* (2013.01); *A61Q 13/00* (2013.01); *A61Q 19/00* (2013.01); *C11B 9/00* (2013.01); *C11D 3/50* (2013.01)

(58) Field of Classification Search
None
See application file for complete search history.

(56) References Cited

U.S. PATENT DOCUMENTS

| | | | |
|---|---|---|---|
| 6,046,156 A | 4/2000 | Perry | |
| 6,075,111 A * | 6/2000 | Perry | A61K 8/895 424/401 |
| 6,077,923 A | 6/2000 | Perry et al. | |
| 6,153,578 A | 11/2000 | Perry | |
| 2002/0054893 A1 | 5/2002 | Ishida et al. | |
| 2002/0077508 A1 | 6/2002 | Gautschi et al. | |
| 2003/0125220 A1 | 7/2003 | Dykstra et al. | |
| 2005/0014663 A1 | 1/2005 | Dykstra et al. | |
| 2005/0227879 A1 | 10/2005 | Dykstra et al. | |
| 2016/0075628 A1 | 3/2016 | Gerke et al. | |

FOREIGN PATENT DOCUMENTS

| | | |
|---|---|---|
| JP | 04-337395 A | 11/1992 |
| JP | 04-368352 A | 12/1992 |
| JP | 2000-109489 A | 4/2000 |
| JP | 2000-119395 A | 4/2000 |
| JP | 2001-303091 A | 10/2001 |
| JP | 2002-088391 A | 3/2002 |
| JP | 2005-502768 A | 1/2005 |
| JP | 2009-249468 A | 10/2009 |

OTHER PUBLICATIONS

ISR References—PCT/JP2017/027948 (Year: 2017).*
Ishida & Mukaiyama, "A New Method for the Preparation of σ-Alkoxy-α, β-unsaturated Aldehydes and Polyenals", Bulletin of the Chemical Society of Japan, vol. 50 (5), May 1977, pp. 1161-1168 (8 pages total).
Cazeau et al., "A New Practical Synthesis of Silyl Enol Ethers", Tetrahedron, vol. 43, No. 9, 1987, pp. 2089-2100 (10 pages total).
International Search Report (PCT/ISA/210) dated Aug. 29, 2017 issued by the International Searching Authority in International Application No. PCT/JP2 017/027948.
Written Opinion (PCT/ISA/237) dated Aug. 29, 2017 issued by the International Searching Authority in International Application No. PCT/JP2 017/027948.

* cited by examiner

*Primary Examiner* — Clinton A Brooks
*Assistant Examiner* — Kofi Adzamli
(74) *Attorney, Agent, or Firm* — Sughrue Mion, PLLC

(57) ABSTRACT

The present invention relates to a method for releasing an unsaturated aldehyde or ketone represented by the general formula (2) by irradiating the compound represented by the general formula (1) with light, in which the compound represented by the general formula (1) is used as a flavor or fragrance precursor:

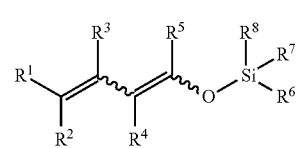

(1)

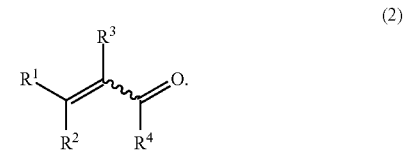

(2)

7 Claims, No Drawings

METHOD FOR RELEASING UNSATURATED ALDEHYDE OR KETONE

TECHNICAL FIELD

The present invention relates to a flavor or fragrance precursor which releases an unsaturated aldehyde or ketone by the action of light.

BACKGROUND ART

In recent years, with an increase of consumer's interest in fragrance, a demand for the fragrance at the time of using the product ranges widely. With respect to the needs for improvements in persistence of fragrance, in general, compounded flavors or fragrances or flavor or fragrance capsules, in which a lot of a last note with low volatility is blended, are used. In addition, as a persistence enhancing agent of fragrance, there are proposed fixatives, for example, p-menthane-3,8-diol (see Patent Literature 1) and 3-(menthoxy)-1,2-propanediol (see Patent Literature 2).

However, the feeling to fragrance is different among individuals and is influenced by physical condition, etc. Thus, there was a case where when the fragrance is unnecessarily given over a long time, the feeling is offended, or a feeling of displeasure is brought.

In addition to the consumer's needs for enjoying the fragrance over a long time, there are a large number of consumer's needs for enjoying the fragrance only when necessary.

CITATION LIST

Patent Literature

Patent Literature 1: JP-A-4-337395
Patent Literature 2: JP-A-2002-88391

SUMMARY OF INVENTION

Technical Problem

A problem of the present invention is to develop a flavor or fragrance precursor capable of emitting an aroma component at some opportunity in daily living.

Solution to Problem

In order to solve the foregoing problem, the present inventors made extensive and intensive investigations. As a result, it has been found that a compound having a specified structure is able to release an aromatic unsaturated aldehyde or ketone by the action of light, thereby leading to accomplishment of the present invention.

Specifically, the present invention is concerned with the following [1] to [7].

[1] A method for releasing an unsaturated aldehyde or ketone represented by the general formula (2) by irradiating the compound represented by the general formula (1) with light, in which the compound represented by the general formula (1) is used as a flavor or fragrance precursor.

[Chem. 1]

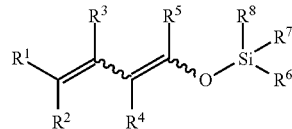

In the formula, $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group: $R^1$ and $R^2$, $R^1$ and $R^3$, $R^1$ and $R^4$, $R^1$ and $R^5$, $R^3$ and $R^4$, or $R^3$ and $R^5$ may together form a ring; and a wavy line expresses either one of E and Z geometric isomers or a mixture thereof.

[Chem. 2]

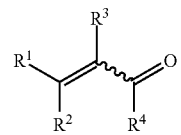

In the formula, $R^1$, $R^2$, $R^3$, $R^4$, and the wavy line are the same as defined above for the general formula (1); and $R^1$ and $R^2$, $R^1$ and $R^3$, $R^1$ and $R^4$, or $R^3$ and $R^4$ may together form a ring.

[2] The method for releasing an unsaturated aldehyde or ketone as set forth in [1], wherein a wavelength of the light used is 280 to 780 nm.

[3] The method for releasing an unsaturated aldehyde or ketone as set forth in [1] or [2], wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

[4] A flavor or fragrance composition containing a compound represented by the general formula (1).

[Chem. 3]

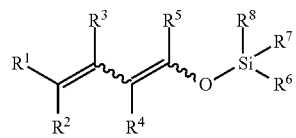

In the formula, $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group; $R^1$ and $R^2$, $R^1$ and $R^3$, $R^1$ and $R^4$, $R^1$ and $R^5$, $R^3$ and $R^4$, or $R^3$ and $R^5$ may together form a ring; and a wavy line expresses either one of E and Z geometric isomers or a mixture thereof.

[5] The flavor or fragrance composition as set forth in [4], wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

[6] An aroma product, a laundry care product, a hair care product, a cosmetic, or a cleaner comprising a compound represented by the general formula (1).

[Chem. 4]

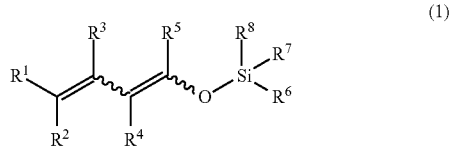

(1)

In the formula, $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group; $R^1$ and $R^2$, $R^1$ and $R^3$, $R^1$ and $R^4$, $R^1$ and $R^5$, $R^3$ and $R^4$, or $R^3$ and $R^5$ may together form a ring; and the wavy line expresses either one of E and Z geometric isomers or a mixture thereof.

[7] The aroma product, the laundry care product, the hair care product, the cosmetic, or the cleaner as set forth in [6], wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

Advantageous Effects of Invention

The compound represented by the general formula (1) according to the present invention is able to release an aroma unsaturated aldehyde or ketone by the action of light. In addition, by containing the compound represented by the general formula (1), it is possible to provide a flavor or fragrance composition, an aroma product, a laundry care product, a hair care product, a cosmetic, or a cleaner, each of which emits an aroma when allowing light to act.

DESCRIPTION OF EMBODIMENTS

The present invention is hereunder described in detail.

In the present invention, by using a compound represented by the general formula (1) as a flavor or fragrance precursor and irradiating the compound with light, an α,β-unsaturated aldehyde or an α,β-unsaturated ketone, which is a compound represented by the general formula (2) as a flavor or fragrance component, can be emitted.

The compound represented by the general formula (1) and the compound represented by the general formula (2) are described.

Compound represented by the general formula (1):

[Chem. 5]

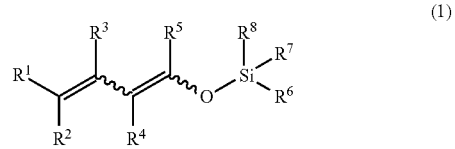

(1)

In the formula, $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group. The wavy line expresses either one of E and Z geometric isomers or a mixture thereof.

In addition, $R^1$ and $R^2$, $R^1$ and $R^3$, $R^1$ and $R^4$, $R^1$ and $R^5$, $R^3$ and $R^4$, or $R^3$ and $R^4$ may together form a ring.

Compound represented by the general formula (2):

[Chem. 6]

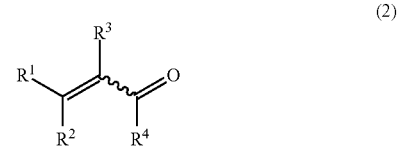

(2)

In the formula, $R^1$, $R^2$, $R^3$, $R^4$, and the wavy line are the same as defined above for the general formula (1).

In addition, $R^1$ and $R^2$, $R^1$ and $R^3$, $R^1$ and $R^4$, or $R^3$ and $R^4$ may together form a ring.

The alkyl group, the cycloalkyl group, the alkenyl group, the aryl group, the aralkyl group, the aromatic heterocyclic group, the aliphatic heterocyclic group, the acyl group, and the alkoxycarbonyl group, each of which is represented by $R^1$, $R^2$, $R^3$, $R^4$, $R^5$, $R^6$, $R^7$, and $R^8$, are described. Each of these groups may have a substituent group.

Examples of the alkyl group include a straight chain or branched alkyl group having 1 to 30 carbon atoms, preferably 1 to 10 carbon atoms. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a heneicosyl group, a docosyl group, etc.

Examples of the cycloalkyl group include a cyclopropyl group, a cyclobutyl group, a cyclopentyl group, a cyclohexyl group, etc.

Examples of the alkenyl group include a straight chain or branched alkenyl group having 2 to 20 carbon atoms, preferably 2 to 10 carbon atoms, and a cyclic alkenyl group having 3 to 20 carbon atoms, preferably 5 to 10 carbon atoms. Specifically, examples of the alkenyl group include a vinyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-cyclopentenyl group, a 3-cyclopentenyl group, a 1-hexenyl group, a 2-hexenyl group, a 3-hexenyl group, a 4-hexenyl group, a 5-hexenyl group, a 4-methyl-3-pentenyl group, a 4,8-dimethyl-3,7-nonadienyl group, a 1-cyclohexenyl group, a 3-cyclohexenyl group, etc.

Examples of the aryl group include an aryl group having 6 to 14 carbon atoms. Specifically, examples thereof include a phenyl group, a naphthyl group, an anthryl group, a phenanthryl group, a biphenyl group, etc.

As the aralkyl group, for example, an aralkyl group having 7 to 12 carbon atoms is preferred. Specifically, examples thereof include a benzyl group, a 2-phenylethyl group, a 1-phenylpropyl group, a 3-naphthylpropyl group, etc.

Examples of the aromatic heterocyclic group include a group having 2 to 15 carbon atoms and containing, as a hetero atom, at least one, and preferably 1 to 3 nitrogen atoms, oxygen atoms, or sulfur atoms. Preferably, examples thereof include a 5- or 6-membered monocyclic aromatic heterocyclic group and a polycyclic or condensed ring aromatic heterocyclic group. Specific examples of the aromatic heterocyclic group include a furyl group, a methylfuryl group, a thienyl group, a pyridyl group, a pyrimidinyl group, a pyrazinyl group, a pyridazinyl group, a pyrazolinyl group, an imidazolyl group, an oxazolinyl group, a thiazolinyl group, a benzofuryl group, a benzothienyl group, a quinolyl group, an isoquinolyl group, a quinoxalinyl group, a phtharazinyl group, a quinazolinyl group, a naphthylidinyl group, a cinnolinyl group, a benzimidazolyl group, a benzoxazolyl group, a benzothiazolyl group, etc.

Examples of the aliphatic heterocyclic group include a group having 2 to 14 carbon atoms and containing, as a hetero atom, at least one, and preferably 1 to 3 nitrogen atoms, oxygen atoms, or sulfur atoms. Preferably, examples thereof include a 5- or 6-membered monocyclic aliphatic heterocyclic group and a polycyclic or condensed ring aliphatic heterocyclic group. Specific examples of the aliphatic heterocyclic group include a 2-oxo-1-pyrrolidinyl group, a piperidino group, a piperazinyl group, a morpholino group, a tetrahydrofuryl group, a tetrahydropyranyl group, a tetrahydrothienyl group, etc.

Examples of the acyl group include an acetyl group, a propanoyl group, a butanoyl group, an octanoyl group, a benzoyl group, a toluoyl group, a xyloyl group, a naphthoyl group, a phenanthroyl group, an anthroyl group, etc.

As the alkoxycarbonyl group, for example, an alkoxycarbonyl group having 1 to 30 carbon atoms is preferred. Specifically, examples thereof include a methoxycarbonyl group, an ethoxycarbonyl group, a n-propoxycarbonyl group, an isopropoxycarbonyl group, a n-butoxycarbonyl group, a 2-butoxycarbonyl group, an isobutoxycarbonyl group, a tert-butoxycarbonyl group, a n-pentyloxycarbonyl group, a 2-methylbutoxycarbonyl group, a 3-methylbutoxycarbonyl group, a 2,2-dimethylpropoxycarbonyl group, a n-hexyloxycarbonyl group, a 2-methylpentyloxycarbonyl group, a 3-methylpentyloxycarbonyl group, a 4-methylpentyloxycarbonyl group, a 5-methylpentyloxycarbonyl group, a cyclopentyloxycarbonyl group, a cyclohexyloxycarbonyl group, a dicyclopentylmethoxycarbonyl group, a dicyclohexylmethoxycarbonyl group, a tricyclopentylmethoxycarbonyl group, a tricyclohexylmethoxycarbonyl group, a phenylmethoxycarbonyl group, a diphenylmethoxycarbonyl group, a triphenylmethoxycarbonyl group, etc.

Each of the groups other than a hydrogen atom, which are represented by $R^1$ to $R^8$, may have a substituent group. Examples of the substituent group include an alkenyl group, an alkynyl group, an aryl group, an aliphatic heterocyclic group, an aromatic heterocyclic group, an alkoxy group, an alkylenedioxy group, an aryloxy group, an aralkyloxy group, a heteroaryloxy group, an amino group, a substituted amino group, a nitro group, a cyano group, an alkoxycarbonyl group, a halogen atom, an alkyl halide group, etc.

The alkenyl group as the substituent group for $R^1$ to $R^8$ may be a straight chain or branched alkenyl group. Examples thereof include an alkenyl group having 2 to 20 carbon atoms, preferably 2 to 10 carbon atoms, and more preferably 2 to 6 carbon atoms. Specifically, examples thereof include a vinyl group, a propenyl group, a 1-butenyl group, a pentenyl group, a hexenyl group, etc.

The alkynyl group as the substituent group for $R^1$ to $R^8$ may be a straight chain or branched alkynyl group. Example thereof include an alkynyl group having 2 to 15 carbon atoms, preferably 2 to 10 carbon atoms, and more preferably 2 to 6 carbon atoms. Specifically, examples thereof include an ethynyl group, a 1-propynyl group, a 2-propynyl group, a 1-butynyl group, a 3-butynyl group, a pentynyl group, a hexynyl group, etc.

Examples of the aryl group as the substituent group for $R^1$ to $R^8$ include an aryl group having 6 to 14 carbon atoms. Specifically, examples thereof include a phenyl group, a naphthyl group, an anthryl group, a phenanthryl group, a biphenyl group, a tolyl group, a xylyl group, a mesityl group, a methoxyphenyl group, a dimethoxyphenyl group, a fluorophenyl group, etc.

Examples of the aliphatic heterocyclic group as the substituent group for $R^1$ to $R^8$ include a group having 2 to 14 carbon atoms and containing, as a hetero atom, at least one, and preferably 1 to 3 nitrogen atoms, oxygen atoms, or sulfur atoms. Preferably, examples thereof include a 5- or 6-membered monocyclic aliphatic heterocyclic group and a polycyclic or condensed ring aliphatic heterocyclic group. Specific examples of the aliphatic heterocyclic group include a 2-oxo-1-pyrrolidinyl group, a piperidino group, a piperazinyl group, a morpholino group, a tetrahydrofuryl group, a tetrahydropyranyl group, a tetrahydrothienyl group, etc.

Examples of the aromatic heterocyclic group as the substituent group for $R^1$ to $R^8$ include a group having 2 to 15 carbon atoms, and preferably 3 to 11 carbon atoms and containing, as a hetero atom, at least one, and preferably 1 to 3 nitrogen atoms, oxygen atoms, or sulfur atoms. Preferably, examples thereof include a 5- or 6-membered monocyclic aromatic heterocyclic group and a polycyclic or condensed ring aromatic heterocyclic group. Specific examples of the aromatic heterocyclic group include a furyl group, a thienyl group, a pyridyl group, a pyrimidinyl group, a pyrazinyl group, a pyridazinyl group, a pyrazolinyl group, an imidazolyl group, an oxazolinyl group, a thiazolinyl group, a benzofuryl group, a benzothienyl group, a quinolyl group, an isoquinolyl group, a quinoxalinyl group, a phtharazinyl group, a quinazolinyl group, a naphthylidinyl group, a cinnolinyl group, a benzimidazolyl group, a benzoxazolyl group, a benzothiazolyl group, etc.

Examples of the alkoxy group as the substituent group for $R^1$ to $R^8$ include a straight chain or branched alkoxy group having 1 to 6 carbon atoms. Specifically, examples thereof include a methoxy group, an ethoxy group, a n-propoxy group, an isopropoxy group, a n-butoxy group, a 2-butoxy group, an isobutoxy group, a tert-butoxy group, a n-pentyloxy group, a 2-methylbutoxy group, a 3-methylbutoxy group, a 2,2-dimethylpropoxy group, a n-hexyloxy group, a 2-methylpentyloxy group, a 3-methylpentyloxy group, a 4-methylpentyloxy group, a 5-methylpentyloxy group, etc.

Examples of the alkylenedioxy group as the substituent group for $R^1$ to $R^8$ include an alkylenedioxy group having 1 to 3 carbon atoms. Specifically, examples thereof include a methylenedioxy group, an ethylenedioxy group, a propylenedioxy group, an isopropylidenedioxy group, etc.

Examples of the aryloxy group as the substituent group for $R^1$ to $R^8$ include an aryloxy group having 6 to 14 carbon atoms. Specifically, examples thereof include a phenoxy group, a naphthyloxy group, n anthryloxy group, etc.

Examples of the aralkyloxy group as the substituent group for $R^1$ to $R^8$ include an aralkyloxy group having 7 to 12 carbon atoms. Specifically, examples thereof include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, a 3-phenylhexyloxy group, a 4-phenylhexyloxy group, a 5-phenylhexyloxy group, a 6-phenylhexyloxy group, etc.

Examples of the heteroaryloxy group as the substituent group for $R^1$ to $R^8$ include a heteroaryloxy group containing, as a hetero atom, at least one, and preferably 1 to 3 nitrogen atoms, oxygen atoms, or sulfur atoms and having 2 to 14 carbon atoms. Specifically, examples thereof include a 2-pyridyloxy group, a 2-pyrazyloxy group, a 2-pyrimidyloxy group, a 2-quinolyloxy group, etc.

Examples of the substituted amino group as the substituent group for $R^1$ to $R^8$ include mono- or dialkylamino groups, such as a N-methylamino group, an N,N-dimethylamino group, an N,N-diethylamino group, an N,N-diisopropylamino group, and an N-cyclohexylamino group; mono- or diarylamino groups, such as an N-phenylamino group, an N,N-diphenylamino group, an N-naphthylamino group, and an N-naphthyl-N-phenylamino group; and mono- or diaralkylamino groups, such as an N-benzylamino group and an N,N-dibenzylamino group; etc.

As the alkoxycarbonyl group as the substituent group for $R^1$ to $R^8$, for example, an alkoxycarbonyl group having 1 to 30 carbon atoms is preferred. Specifically, examples thereof include a methoxycarbonyl group, an ethoxycarbonyl group, a n-propoxycarbonyl group, an isopropoxycarbonyl group, a n-butoxycarbonyl group, a 2-butoxycarbonyl group, an isobutoxycarbonyl group, a tert-butoxycarbonyl group, a n-pentyloxycarbonyl group, a 2-methylbutoxycarbonyl group, a 3-methylbutoxycarbonyl group, a 2,2-dimethylpropoxycarbonyl group, a n-hexyloxycarbonyl group, a 2-methylpentyloxycarbonyl group, a 3-methylpentyloxycarbonyl group, a 4-methylpentyloxycarbonyl group, a 5-methylpentyloxycarbonyl group, a cyclopentyloxycarbonyl group, a cyclohexyloxycarbonyl group, a dicyclopentylmethoxycarbonyl group, a dicyclohexylmethoxycarbonyl group, a tricyclopentylmethoxycarbonyl group, a tricyclohexylmethoxycarbonyl group, a phenylmethoxycarbonyl group, a diphenylmethoxycarbonyl group, a triphenylmethoxycarbonyl group, etc.

Examples of the halogen atom as the substituent group for $R^1$ to $R^8$ include a fluorine atom, a chlorine atom, a bromine atom, an iodine atom, etc.

As the alkyl halide group as the substituent group for $R^1$ to $R^8$, for example, a perhalogenoalkyl group having 1 to 10 carbon atoms is preferred. Examples thereof include a trifluoromethyl group, a pentafluoroethyl group, a heptafluoropropyl group, an undecafluoropentyl group, a heptadecafluorooctyl group, an undecafluorocyclohexyl group, a dichloromethyl group, etc.

In the compound represented by the general formula (1), examples of the ring which $R^1$ and $R^2$, $R^1$ and $R^3$, $R^1$ and $R^4$, $R^1$ and $R^5$, $R^3$ and $R^4$, or $R^3$ and $R^5$ form together include a cyclopentane ring, a cyclohexane ring, an indane ring, a tetralin ring, a cyclopentene ring, a cyclohexene ring, a cycloheptene ring, an indene ring, a dihydronaphthalene ring, an octahydronaphthalene ring, a decahydronaphthalene ring, etc. These rings may be substituted with the aforementioned alkyl group or the like.

In the compound represented by the general formula (2), examples of the ring which $R^1$ and $R^2$, $R^1$ and $R^3$, $R^1$ and $R^4$, or $R^3$ and $R^4$ form together include a cyclopentane ring, a cyclohexane ring, an indane ring, a tetralin ring, a cyclopentene ring, a cyclohexene ring, a cycloheptene ring, an indene ring, a dihydronaphthalene ring, an octahydronaphthalene ring, a decahydronaphthalene ring, etc. These rings may be substituted with the aforementioned alkyl group or the like.

Among those described above, $R^1$, $R^2$, $R^3$, $R^4$, $R^5$, $R^6$, $R^7$, and $R^8$ are each preferably a hydrogen atom or an alkyl group having 10 or less carbon atoms, which may have a substituent group.

As the alkyl group having 10 or less carbon atoms, for example, a straight chain or branched alkyl group having 1 to 10 carbon atoms is preferred. Specifically, examples thereof include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a heptyl group, an octyl group, a nonyl group, a decyl group, etc.

As for a more preferred example of $R^1$, $R^2$, $R^3$, $R^4$, $R^5$, $R^6$, $R^7$, and $R^8$, $R^1$ is an alkyl group having 1 to 6 carbon atoms, which may have a substituent group; $R^2$, $R^3$, $R^4$, and $R^5$ are each a hydrogen atom or a methyl group; and $R^6$, $R^7$, and $R^8$ are each an alkyl group having 1 to 6 carbon atoms, which may have a substituent group.

Specifically, examples of the alkyl group having 1 to 6 carbon atoms include a methyl group, an ethyl group, a n-propyl group, an isopropyl group, a n-butyl group, a 2-butyl group, an isobutyl group, a tert-butyl group, a n-pentyl group, a 2-pentyl group, a 3-pentyl group, a tert-pentyl group, a 2-methylbutyl group, a 3-methylbutyl group, a 2,2-dimethylpropyl group, a 1,2-dimethylpropyl group, a n-hexyl group, a 2-hexyl group, a 3-hexyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, etc.

In the present invention, the compound represented by the general formula (1), which is used as the flavor or fragrance precursor, is preferably one prepared from an α,β-unsaturated aldehyde having 6 to 14 carbon atoms.

Specific examples of the compound represented by the general formula (1) according to the present invention include the compounds shown below. In the compound represented by the general formula (1), the wavy line expresses either one of E and Z geometric isomers or a mixture thereof.

[Chem. 7]

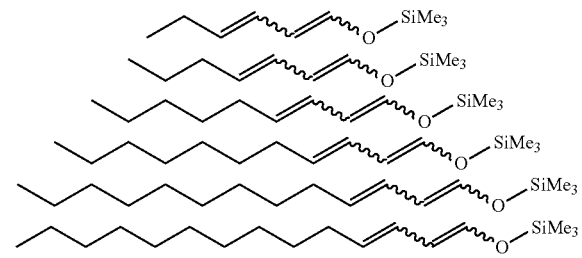

[Chem. 8]

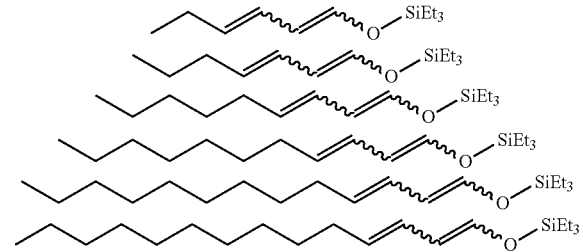

[Chem. 9]

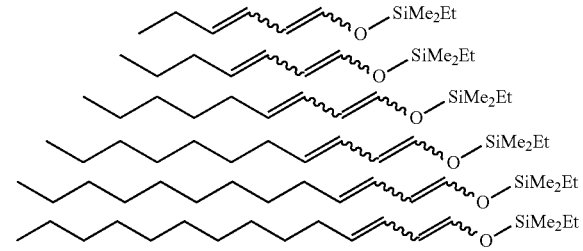

In the aforementioned formulae, Me represents a methyl group, and Et represents an ethyl group.

The compound represented by the general formula (1), which is used in the present invention, can be readily synthesized by an already-known method. Among the compounds represented by the general formula (1), a production method of triethyl(1,3-hexadienyloxy)silane represented by the formula (4) shown below is described.

The compound represented by the general formula (1) can be, for example, synthesized according to the methods described in Bull. Chem. Soc. Jpn. 1977, 50, 1161-1168 and Tetrahedron 1987, 43, 2089-2100. The foregoing methods can be expressed by the following Scheme 1.

Scheme 1

[Chem. 10]

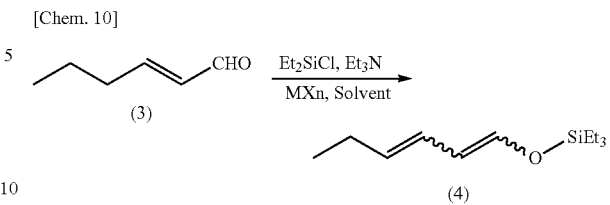

In the Scheme 1, the compound represented by the formula (4) can be synthesized according to the method described in Tetrahedron 1987, 43, 2089-2100.

As for the synthesis of the compound represented by the formula (4), the compound can be prepared by dropping chlorotriethylsilane in a solution of 2-hexenal (compound of the formula (3)), triethylamine, and a metal halide compound represented by a general formula $MX_n$ dissolved in an organic solvent and allowing the contents to react with each other at a temperature ranging from 0 to 120° C. Examples of the metal halide compound represented by the general formula $MX_n$ include LiBr, LiI, NaBr, NaI, $ZnCl_2$, $ZnBr_2$, $ZnI_2$, etc. NaI or $ZnCl_2$ is preferred.

The obtained compound represented by the formula (4) can be isolated in the usual manner, for example, extraction, recrystallization, or chromatography of every sort.

The compound represented by the general formula (1) according to the present invention can be used as a flavor or fragrance precursor. By irradiating the compound represented by the general formula (1) with light, an α,β-unsaturated aldehyde or an α,β-unsaturated ketone represented by the general formula (2), which is a flavor or fragrance component, can be released.

A wavelength of the irradiation light is preferably 280 to 780 nm, and sunlight is also inclusive.

The compound represented by the general formula (1) according to the present invention can be blended in a flavor or fragrance composition.

Though the compound represented by the general formula (1) can be used alone, it can also be used properly in combination with a known flavor or fragrance component. Examples of the known flavor or fragrance component include natural essential oils, such as lemon oil, orange oil, lime oil, bergamot oil, lavandin oil, lavender oil, geranium oil, rose oil, and sandalwood oil; hydrocarbons, such as α-pinene, β-pinene, limonene, p-cymene, and thujone; aliphatic alcohols, such as octanol and p-tert-butylcyclohexanol; terpene-based alcohols, such as menthol, citronellol, and geraniol: aromatic alcohols, such as benzyl alcohol and phenylethyl alcohol; aliphatic aldehydes: terpene-based aldehydes; aromatic aldehydes; acetals; chain ketones: cyclic ketones, such as damascone, β-ionone, and methylionone; terpene-based ketones, such as carvone, menthone, isomenthone, and camphor: aromatic ketones, such as acetophenone and raspberry ketone; ethers, such as dibenzyl ether; oxides, such as linalool oxide and rose oxide; musks, such as cyclopentadecanolide and cyclohexadecanolide; lactones, such as γ-nonalactone, γ-undecalactone, and coumarin: aliphatic esters, such as an acetic acid ester and a propionic acid ester; aromatic esters, such as a benzoic acid ester and a phenylacetic acid ester; etc.

For the fragrance composition of the present invention, a solvent, such as ethanol, dipropylene glycol (hereinafter also abbreviated as "DPG"), diethyl phthalate, propylene glycol, triethyl citrate, benzyl benzoate, glycerin, triacetin, and triethyl citrate, may be used. In addition, a known component, such as a solubilizing agent and a stabilizing agent, may be further mixed, as necessary.

The compound represented by the general formula (I) according to the present invention can be used for products, such as an aroma product, a laundry care product, a hair care product, a cosmetic, and a cleaner.

Examples of the aroma product include a perfume, eau de cologne, a liquid air freshener, a gel air freshener, a powder air freshener, a beads air freshener, an impregnated air freshener, a mist spray air freshener, an aerosol spray air freshener, a plug-in air freshener, etc.

Examples of the laundry care product include a mist spray for clothing, a detergent, a fabric softener, etc.

Examples of the hair care product include a hair shampoo, a hair rinse, a hair conditioner, a hair treatment, a hair styling agent, etc.

Examples of the cosmetic include a lotion, a milky lotion, a cosmetic cream, a liquid soap, etc.

Examples of the cleaner include a cleaner for toilet, a cleaner for glass, etc.

Since the compound represented by the general formula (1) according to the present invention releases a flavor or fragrance component upon irradiation with light, it is useful to blend the compound represented by the general formula (1) in a product in an environment where after the product is used, it is irradiated with light.

The blending amount of the compound represented by the general formula (1) according to the present invention in each product is not strictly restricted, and it is variable with its application. The blending amount of the compound represented by the general formula (1) according to the present invention in each product is preferably 0.0001 to 10% by weight, and more preferably 0.001 to 5% by weight.

EXAMPLES

The present invention is hereunder specifically described by reference to Examples, but it should be construed that the present invention is by no means limited by these Examples.

Example 1

Synthesis of triethyl(1,3-hexadienyloxy)silane

To a solution of trans-2-hexenal 6.93 mL (60 mmol), triethylamine 10.5 mL (75 mmol) and zinc bromide 1.35 g (6 mmol) in 40 mL of toluene, triethylchlorosilane 10.6 mL (63 mmol) was added dropwise at room temperature, followed by stirring at 110° C. (oil bath) for 24 hours. After quenching the reaction solution with a saturated sodium hydrogencarbonate aqueous solution, the resultant was extracted with toluene, and the resulting organic layer was washed three times with water. After drying the organic layer over sodium sulfate, the filtrate was concentrated under reduced pressure to obtain a crude product. The resulting crude product was purified by silica gel column chromatography to obtain 1.76 g of the target product.

Example 2

Synthesis of triethyl(1,3-hexadienyloxy)silane

To a solution of trans-2-hexenal 23.1 mL (200 mmol), triethylamine 41.8 mL (300 mmol) and sodium iodide 42.0 g (280 mmol) in 200 mL of acetonitrile, triethylchlorosilane 18.8 mL (112 mmol) was added dropwise at 0° C., followed by stirring at room temperature for 2 days. After quenching the reaction solution with a saturated sodium hydrogencarbonate aqueous solution, the resultant was extracted with hexane, and the resulting organic layer was washed three times with water. After drying the organic layer over sodium sulfate, the filtrate was concentrated under reduced pressure to obtain a crude product. The resulting crude product was purified by distillation under reduced pressure (64-68° C./107 Pa) to obtain 10.05 g of the target product.

Example 3

Synthesis of triethyl(1,3-heptadienyloxy)silane

To a solution of trans-2-heptenal 8.97 g (80 mmol), triethylamine 16.7 mL (120 mmol) and sodium iodide 16.8 g (112 mmol) in 100 mL of acetonitrile, triethylchlorosilane 18.8 mL (112 mmol) was added dropwise at 0° C. followed by stirring at room temperature for 2 days. After quenching the reaction solution with a saturated sodium hydrogencarbonate aqueous solution, the resultant was extracted with hexane, and the resulting organic layer was washed three times with water. After drying the organic layer over sodium sulfate, the filtrate was concentrated under reduced pressure to obtain a crude product. The resulting crude product was purified by distillation under reduced pressure (70-82° C./133 Pa) to obtain 7.21 g of the target product.

Example 4

Synthesis of triethyl(1,3-octadienyloxy)silane

To a solution of trans-2-octenal 12.62 g (100 mmol), triethylamine 19.5 mL (140 mmol) and sodium iodide 8.99 g (60 mmol) in 70 mL of acetonitrile, triethylchlorosilane 20.1 mL (120 mmol) was added dropwise at 0° C., followed by stirring at room temperature for 2 days. After quenching the reaction solution with methanol, the resultant was extracted with hexane, and the hexane layer was concentrated under reduced pressure to obtain a crude product. The resulting crude product was purified by distillation under reduced pressure (89-92° C./80 Pa) to obtain 12.89 g of the target product.

Comparative Example 1

Synthesis of triethyl(1-hexenyloxy)silane

To a solution of hexenal 9.77 mL (80 mmol), triethylamine 15.6 mL (112 mmol) and sodium iodide 7.19 g (48 mmol) in 56 mL of acetonitrile, triethylchlorosilane 16.1 mL (96 mmol) was added dropwise at 0° C., followed by stirring at room temperature for 2 days. After quenching the reaction solution with methanol, the resultant was extracted with hexane, and the hexane layer was concentrated under reduced pressure to obtain a crude product. The resulting crude product was purified by distillation under reduced pressure (63-67° C./67 Pa) to obtain 7.26 g of the target product.

Comparative Example 2

Synthesis of 3,7-dimethyl-1,6-octadienyl acetate

To a mixture of acetic anhydride 3.27 mL (32 mmol), triethyl amine 3.62 mL (26 mmol), and potassium acetate 118 mg (1.20 mmol), 1-citronellal 3.08 mL (20 mmol) was added dropwise at room temperature, followed by stirring under reflux for 7 hours. After quenching the reaction solution by the addition of toluene and water, the resultant was extracted with toluene, and the resulting organic layer was washed with a saturated sodium hydrogencarbonate aqueous solution and water. After drying the organic layer over sodium sulfate, the filtrate was concentrated under reduced pressure to obtain a crude product. The resulting crude product was purified by silica gel column chromatography to obtain 3.20 g of the target product.

Examples 5 to 6 and Comparative Examples 3 to 4

Light Irradiation Test 100 mg of each of the compounds of Examples 2 to 3 and the compounds of Comparative Examples 1 to 2 was charged in a vial bottle, followed by hermetically sealing the bottle, and was irradiated with light at an irradiance of 60 W/m$^2$ (300 to 400 nm) for 1 hour with a xenon lamp (xenon fade meter XA25, manufactured by Suga Test Instruments Co., Ltd.).

5 g of ethanol was added to the light-irradiated sample, and the resultant was subjected to GC/MS analysis to determine a release amount of an unsaturated aldehyde. The results are shown in Table 1.

(GC/MS Measurement Conditions)
Measuring apparatus: 7890GC/5975 MSD (manufactured by Agilent)
Column: BC-WAX, 50 m×0.25 mm I.D.
Temperature rise: 70° C.→220° C., 4° C./min
Split ratio: 20:1
Injection amount: 1 μL

TABLE 1

|  | Example | | Comparative Example | |
| --- | --- | --- | --- | --- |
|  | 5 | 6 | 3 | 4 |
| Compound used | Example 2 | Example 3 | Comparative Example 1 | Comparative Example 2 |
| Amount of unsaturated aldehyde released by irradiation with light | 1.5 mg | 1 mg | 0 mg | 0 mg |

Unsaturated aldehyde released in Example 5: 2-Pentenal
Unsaturated aldehyde released in Example 6: 2-Hexenal It was confirmed from the results of Table 1 that the compound represented by the general formula (1) according to the present invention releases an unsaturated aldehyde upon irradiation with light and has an effect as a flavor or fragrance precursor.

Example 7

Fragrance Composition for Spray for Clothing

A fragrance composition for spray for clothing was prepared according to a formulation shown in Table 2.

TABLE 2

| Formulation | |
| --- | --- |
|  | Parts by weight |
| Undecylene aldehyde | 5 |
| Allylamyl glycolate | 2 |
| Allyl enanthate | 5 |

TABLE 2-continued

| Formulation | |
| --- | --- |
|  | Parts by weight |
| Benzyl acetate | 10 |
| Borneol | 6 |
| Cinnamic alcohol | 7 |
| Citronellol | 30 |
| Coumarin | 3 |
| Tricyclodecenyl acetate | 80 |
| α-Damascone | 1 |
| Dihydromyrcenol | 60 |
| Diphenyl oxide | 3 |
| Eucalyptus oil | 1 |
| Geraniol | 30 |
| Methyl dihydrojasmonate | 50 |
| Hexyl cinnamic aldehyde | 40 |
| Lime oil | 25 |
| Lemon oil | 30 |
| Linalol | 80 |
| Linalyl acetate | 30 |
| MUSK T (manufactured by Takasago International Corporation) | 100 |
| γ-Methylionone | 20 |
| Methyl nonyl ketone | 2 |
| Nerol | 20 |
| ORBITONE (manufactured by Takasago International Corporation) | 30 |
| 4-t-Butylcyclohexanol | 30 |
| p-t-Butylcyclohexyl acetate | 100 |
| Compound synthesized in Example 2 | 200 |

MUSK T (registered trademark),
ORBITONE (registered trademark)

Examples 8 to 10 and Comparative Examples 5 to 6

Sunlight Exposure Test

Using each of the compounds of Examples 2 and 3, the fragrance composition of Example 7, and the compounds of Comparative Examples 1 and 2, sprays for clothing were prepared according to the formulations shown in Table 3. After spraying 1 g of the spray for clothing on a cotton towel, the cotton towel was exposed to direct sunlight outdoors for 30 minutes (Kanagawa Prefecture, fair weather at a temperature of 22 to 23° C. in May 2016). The fragrance was evaluated by ten expert panelists according to the following criteria. The evaluation score was determined by averaging the evaluated values of the expert panelists. The results are shown in Table 4.

TABLE 3

| Preparation method of spray for clothing | | | | | |
| --- | --- | --- | --- | --- | --- |
|  | Example | | | Comparative Example | |
|  | 8 | 9 | 10 | 5 | 6 |
| Triethyl(1,3-hexadienyloxy)silane (compound synthesized in Example 2) | 0.3 | — | — | — | — |
| Triethyl(1,3-heptadienyloxy)silane (compound synthesized in Example 3) | — | 0.3 | — | — | — |
| Fragrance composition prepared in Example 7 | — | — | 0.5 | — | — |
| Triethyl(1-hexenyloxy)silane (compound synthesized in Comparative Example 1) | — | — | — | 0.3 | — |

TABLE 3-continued

Preparation method of spray for clothing

|  | Example | | | Comparative Example | |
|---|---|---|---|---|---|
|  | 8 | 9 | 10 | 5 | 6 |
| 3,7-Dimethyl-1,6-octadienyl acetate (compound synthesized in Comparative Example 2) | — | — | — | — | 0.3 |
| Polyoxyethylene (60) hydrogenated castor oil | 0.7 | 0.7 | 1.2 | 0.7 | 0.7 |
| 95% ethanol | 15 | 15 | 15 | 15 | 15 |
| Deionized water | 84 | 84 | 83.3 | 84 | 84 |
| Total (% by weight) | 100 | 100 | 100 | 100 | 100 |

(Evaluation Criteria of Odor Intensity at the Time of Sunlight Exposure)
0: Odorless
1: Barely perceptible odor
2: Weak odor can be seen in whether what of smell
3: Odor easily perceivable
4: Strong odor
5: Intense odor
(Comparison Criteria of Odor Intensity with Non-Sunlight Exposure)
1: Same degree as in non-sunlight exposure
2: Slightly strong as compared with non-sunlight exposure
3: Strong as compared with non-sunlight exposure
4: Fairly strong as compared with non-sunlight exposure

TABLE 4

|  | Example | | | Comparative Example | |
|---|---|---|---|---|---|
|  | 8 | 9 | 10 | 5 | 6 |
| Odor intensity at the time of sunlight exposure | 3 | 2.5 | 2.5 | 1 | 1.5 |
| Comparison with non-sunlight exposure | 3 | 3 | 3 | 1 | 1 |

It was confirmed from the results of Table 4 that the compound represented by the general formula (1) according to the present invention releases an unsaturated aldehyde upon exposure with sunlight, and the fragrance becomes strong.

While the present invention has been described in detail and with reference to specific embodiments thereof, it will be apparent to one skilled in the art that various changes and modifications can be made therein without departing from the spirit and scope thereof. The present application is based on a Japanese patent application filed on Aug. 1, 2016 (Japanese Patent Application No. 2016-151468), the entireties of which are incorporated by reference.

INDUSTRIAL APPLICABILITY

Since the compound represented by the general formula (1) according to the present invention is able to release an unsaturated aldehyde or ketone that is a flavor or fragrance component upon irradiation with light, it can be used as a flavor or fragrance precursor and is useful. By blending the compound represented by the general formula (1) according to the present invention in a flavor or fragrance composition or a product of every sort, a flavor or fragrance composition or product capable of releasing an unsaturated aldehyde or ketone that is a flavor or fragrance component upon irradiation with light, such as sunlight, and the compound represented by the general formula (1) according to the present invention has a possibility for use in the flavor or fragrance industry.

The invention claimed is:

1. A method for releasing an unsaturated aldehyde or ketone represented by the general formula (2) by irradiating the compound represented by the general formula (1) with light, in which the compound represented by the general formula (1) is used as a flavor or fragrance precursor:

[Chem. 1]

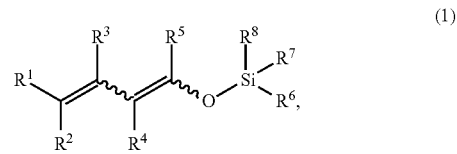

(1)

wherein $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group, $R^1$ and $R^2$, $R^1$ and $R^3$, $R^1$ and $R^4$, $R^1$ and $R^5$, $R^3$ and $R^4$, or $R^3$ and $R^5$ may together form a ring, and a wavy line expresses either one of E and Z geometric isomers or a mixture thereof, and:

[Chem. 2]

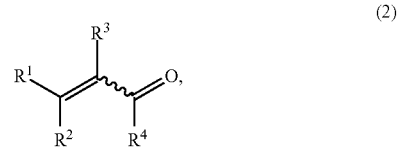

(2)

wherein $R^1$, $R^2$, $R^3$, $R^4$, and a wavy line are the same as defined above for the general formula (1) and $R^1$ and $R^2$, $R^1$ and $R^3$, $R^1$ and $R^4$, or $R^3$ and $R^4$ may together form a ring.

2. The method for releasing an unsaturated aldehyde or ketone according to claim 1, wherein a wavelength of the light used is 280 to 780 nm.

3. The method for releasing an unsaturated aldehyde or ketone according to claim 1, wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

4. A flavor or fragrance composition comprising a compound represented by the general formula (1):

[Chem. 3]

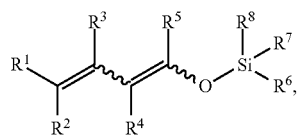

(1)

wherein $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group, $R^1$ and $R^2$, $R^1$ and $R^3$, $R^1$ and $R^4$, $R^1$ and $R^5$, $R^3$ and $R^4$, or $R^3$ and $R^5$ may together form a ring, and a wavy line expresses either one of E and Z geometric isomers or a mixture thereof.

5. The flavor or fragrance composition according to claim 4, wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

6. An aroma product, a laundry care product, a hair care product, a cosmetic, or a cleaner comprising a compound represented by the general formula (1):

[Chem. 4]

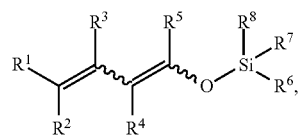

(1)

wherein $R^1$, $R^2$, $R^3$, $R^4$, $R^5$, $R^6$, $R^7$, and $R^8$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an aromatic heterocyclic group which may have a substituent group, an aliphatic heterocyclic group which may have a substituent group, an acyl group which may have a substituent group, or an alkoxycarbonyl group which may have a substituent group, $R^1$ and $R^2$, $R^1$ and $R^3$, $R^1$ and $R^4$, $R^1$ and $R^5$, $R^3$ and $R^4$, or $R^3$ and $R^5$ may together form a ring, and a wavy line expresses either one of E and Z geometric isomers, or a mixture thereof.

7. The aroma product, the laundry care product, the hair care product, the cosmetic, or the cleaner according to claim 6, wherein $R^1$, $R^2$, $R^3$, $R^4$, $R^5$, $R^6$, $R^7$, and $R^8$ are each independently a hydrogen atom or an alkyl group having 10 or less carbon atoms, which may have a substituent group.

* * * * *